(12) United States Patent
Harrison et al.

(10) Patent No.: US 8,136,192 B2
(45) Date of Patent: Mar. 20, 2012

(54) HEAD FOR A POWERED DENTURE BRUSH AND A DENTURE BRUSH INCORPORATING THE SAME

(75) Inventors: James Harrison, Collingwood (CA); Robert G. Dickie, King City (CA)

(73) Assignee: Harrison Hygiene Inc., Barrie, Ontario (CA)

( * ) Notice: Subject to any disclaimer, the term of this patent is extended or adjusted under 35 U.S.C. 154(b) by 400 days.

(21) Appl. No.: 12/410,090

(22) Filed: Mar. 24, 2009

(65) Prior Publication Data

US 2010/0242193 A1 Sep. 30, 2010

(51) Int. Cl.
 *A46B 13/02* (2006.01)
 *A61C 17/22* (2006.01)
(52) U.S. Cl. ............ 15/4; 15/22.1; 15/22.2; 15/28
(58) Field of Classification Search ......... 15/4, 22.1, 15/22.2, 28
See application file for complete search history.

(56) References Cited

U.S. PATENT DOCUMENTS

| | | | | |
|---|---|---|---|---|
| 1,867,896 | A | * | 7/1932 | Soss ............................ 401/46 |
| RE35,941 | E | | 11/1998 | Stansbury, Jr. |
| 5,920,941 | A | | 7/1999 | Iannotta |
| 6,902,397 | B2 | | 6/2005 | Farrell et al. |
| 2002/0116774 | A1 | * | 8/2002 | Forrest ........................ 15/22.1 |
| 2005/0000043 | A1 | * | 1/2005 | Chan et al. ................... 15/22.1 |
| 2008/0189886 | A1 | | 8/2008 | Jimenez |

FOREIGN PATENT DOCUMENTS

CA 2241259 1/2000

* cited by examiner

*Primary Examiner* — Mark Spisich
(74) *Attorney, Agent, or Firm* — Sand & Sebolt

(57) ABSTRACT

A head for a denture brush that is detachably connected to a powered handle and a denture brush incorporating the same. The head includes a housing having a first set of bristles extending outwardly from a first side and a second set of bristles extending outwardly from a second side. The first and second sets of bristles are mounted such that they are movable in response to rotation of a camshaft in the head. Some of bristles on each side of the head may be linearly pulsed toward and away from the housing substantially orthogonally to a longitudinal axis of the head. Additionally, some of the bristles on each side of the head may be rotated about a horizontal axis that is orthogonal to the longitudinal axis.

30 Claims, 11 Drawing Sheets

HEAD FOR A POWERED DENTURE BRUSH AND A DENTURE BRUSH INCORPORATING THE SAME

BACKGROUND OF THE INVENTION

1. Technical Field

This invention generally relates to toothbrushes. More particularly, the invention relates to a powered denture brush. Specifically, the invention relates to a powered denture brush that has a set of powered bristles on both of a first and second side of the head, where some of those bristles may be moved linearly toward and away from the side of the head and others may be rotated about an axis orthogonal to the longitudinal axis of the head.

2. Background Information

It is estimated that somewhere around thirty five-million people in North America have a full or partial set of dentures. The dentures tend to vary quite a bit in size and shape because of the variations in patients' jaws. The most common method of cleaning dentures that is currently in use is to remove the plate from the mouth and to place it into a denture cup holding a cleaning solution. One such suitable cleaning solution is that manufactured and sold under the trademark POLIDENT by Block Drug Company, Inc. of West Trenton, N.J. A manual denture brush may be used in conjunction with the cleaner. As many denture users prefer not to be without their dentures, the manual cleaning approach is much faster and is therefore favored by many. However, manual cleaning requires a significant amount of dexterity and this may present a problem for older denture wearers.

Typical denture brushes have bristles extending outwardly from two opposing sides of the brush head. The bristles are designed for use on opposite sides of the dentures. A set of long pointed bristles extends outwardly from one side of the head and a set of shorter bristles extend outwardly from the other side of the head. The user holds the dentures in one hand and uses the long pointed bristles on the brush to reach into the narrow groove on the tissue fitting side of the denture. The brush movements required for this side of the denture require the user to use semicircular movements to follow the narrow channel in the denture. The teeth-side of the denture requires the user to use the larger, more traditionally shaped bristles to clean the teeth. The teeth-side of the denture is brushed in much the same way that a non-denture wearing person would brush their teeth, with the exception that the dentures are held in one hand.

While these manual brushes are useful for cleaning dentures, they are very difficult for the elderly or the infirm to use. There is therefore a need in the art for an improved denture cleaning brush that makes it quicker and easier to clean both the teeth side and the groove side of a denture.

SUMMARY OF THE INVENTION

The device of the present invention comprises a head for a denture brush that is detachably connected to a powered handle and a denture brush incorporating the same. The head includes a housing having a first set of bristles extending outwardly from a first side and a second set of bristles extending outwardly from a second side. The first and second sets of bristles are mounted such that they are movable in response to rotation of a camshaft in the head. Some of the bristles on each side of the head may be linearly pulsed toward and away from the housing in a direction substantially orthogonal to a longitudinal axis of the head. Additionally, some of the bristles on each side of the head may be rotated about a horizontal axis that is orthogonal to the longitudinal axis. The bristles of the first set of bristles are configured to be longer and pointed so that they more easily fit into the grooved side of a denture. The bristles of the first set are also of varying lengths to more easily clean the bottom and sides of the groove in the denture. The bristles in the second set of bristles are shorter and of substantially the same length. The bristles of the second set of bristles are configured to clean the teeth side of the denture. The brush uses either a pulsating, probing in and out bristle action to clean the narrower tissue-fitting side of the denture or a rotational motion of the bristles to accomplish the same. To clean the teeth side of the denture, the brush of the present invention utilizes powered bristles that may be moved in an in-and-out pulsating motion or a combination of rotational and linear in-and-out motion. Either side of the brush head may also include stationary bristles as well as powered bristles. The powered bristles will seek and probe the crevasses such as between the teeth, and the stationary bristles will help to polish the larger, flatter areas on the teeth.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Referring to FIGS. 1-6 there is shown a first embodiment of a powered denture brush in accordance with the present invention and generally indicated at 10. Brush 10 is designed for cleaning a denture 500 (FIGS. 9 & 10) that has both a teeth side 502 and a grooved side 504. Grooved side 504 is configured to receive a portion of the user's gum tissue therein and to be temporarily bonded thereto by way of a bonding agent.

Figure 10:
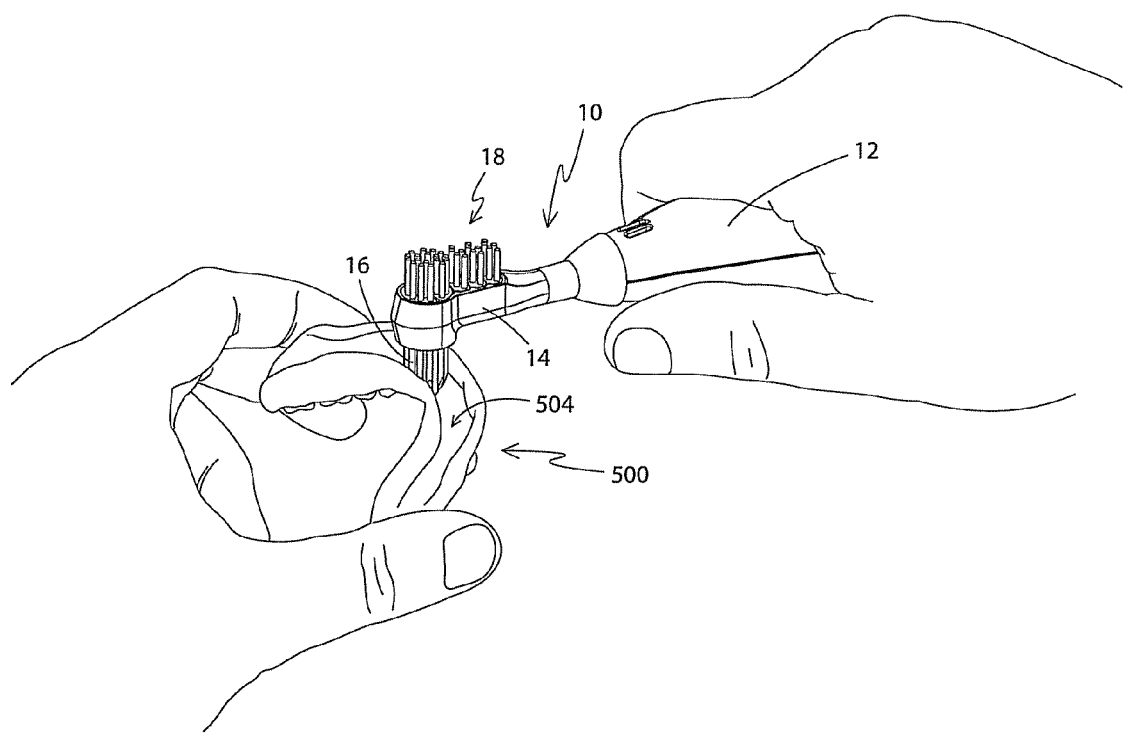
FIG. 10 is a perspective view of the denture brush in use with a second set of bristles being used to clean the groove side of the denture.

Brush 10 comprises a handle 12 and a head 14 that are detachably engageable with each other. As will be hereinafter described in greater detail, handle 12 includes a battery-operated drive mechanism that is operationally connected to components in head 14. Head 14 includes a first set of bristles 16 that extend outwardly away from a first side 14a of head 14 and a second set of bristles 18 that extend outwardly away from a second side 14b of head 14. The first set of bristles 16 is configured to clean gum-receiving groove 504 in a first side of denture 500 (FIG. 10). The second set of bristles 18 is configured to clean the teeth side 502 of denture 500. Preferably, the bristles in the first set of bristles 16 are longer than the bristles in the second set of bristles 18 as they need to be able to reach into groove 504 to clean the same. Preferably, the bristles in the first set of bristles 16 are around 50% longer than the bristles in the second set of bristles 18.

In accordance with a specific feature of the present invention, each of the first and second sets of bristles 16,18 are mounted in the first and second sides 14a, 14b in such a manner that they move relative to the associated first and second sides when the drive mechanism is activated. As will be described herein, that motion may be a linear motion where at least some of the bristles are pulsated in and out relative to the side of the head. Alternatively or additionally, that motion may be a rotational motion where at least some of the bristles rotate about an axis that is orthogonal to a longitudinal axis of the head 14.

A first embodiment of the invention is illustrated in FIGS. 1-6. A second embodiment of the invention is illustrated in FIGS. 7-8. The operation of the brush 10 is illustrated in FIGS. 9 and 10.

Figure 1:
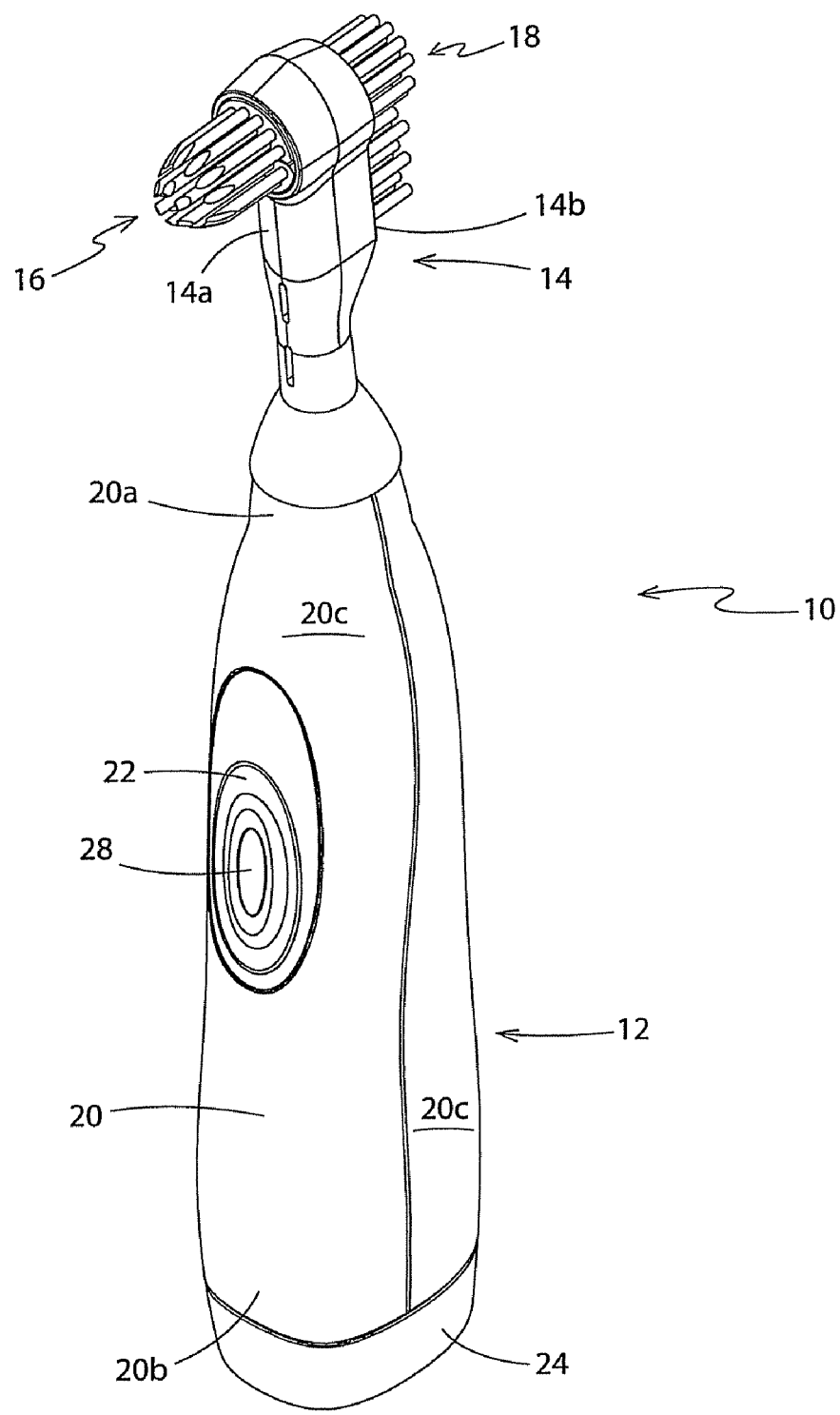
FIG. 1 is a perspective view of a first embodiment of a denture brush in accordance with the present invention.
Figure 2:
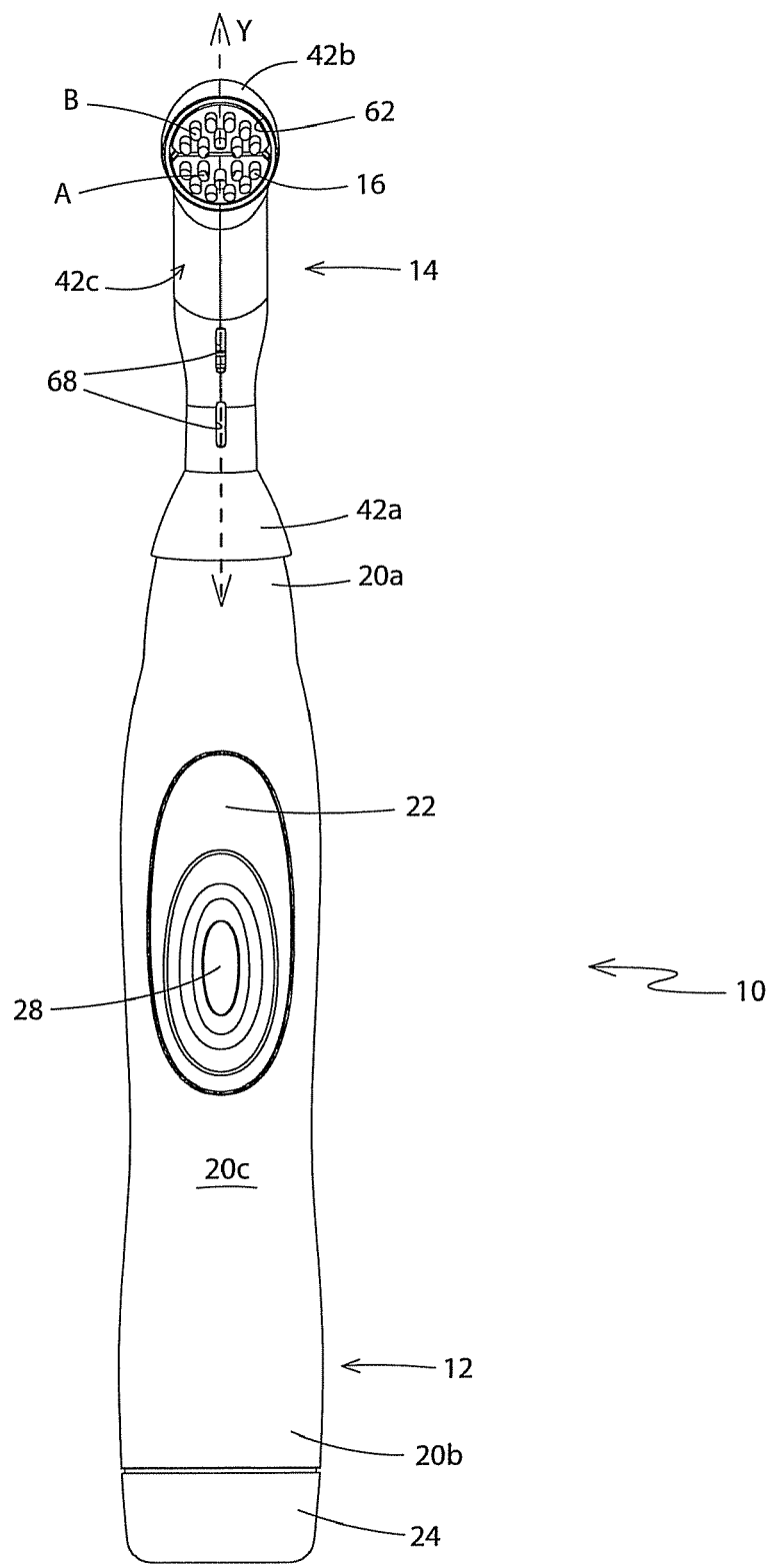
FIG. 2 is a front elevational view of the denture brush of FIG. 1.
Figure 3:
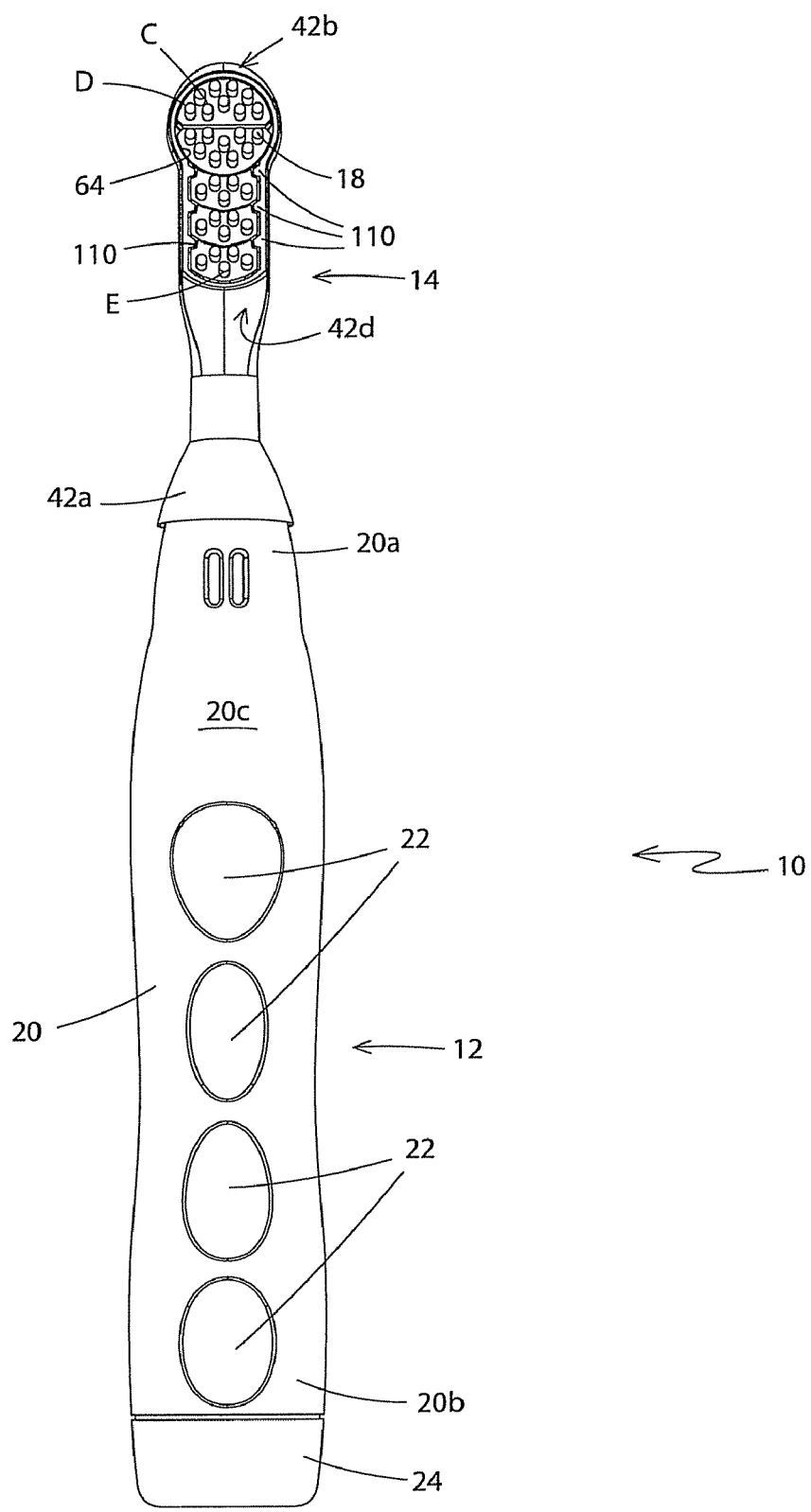
FIG. 3 is a rear elevational view of the denture brush of FIG. 1.
Figure 4:
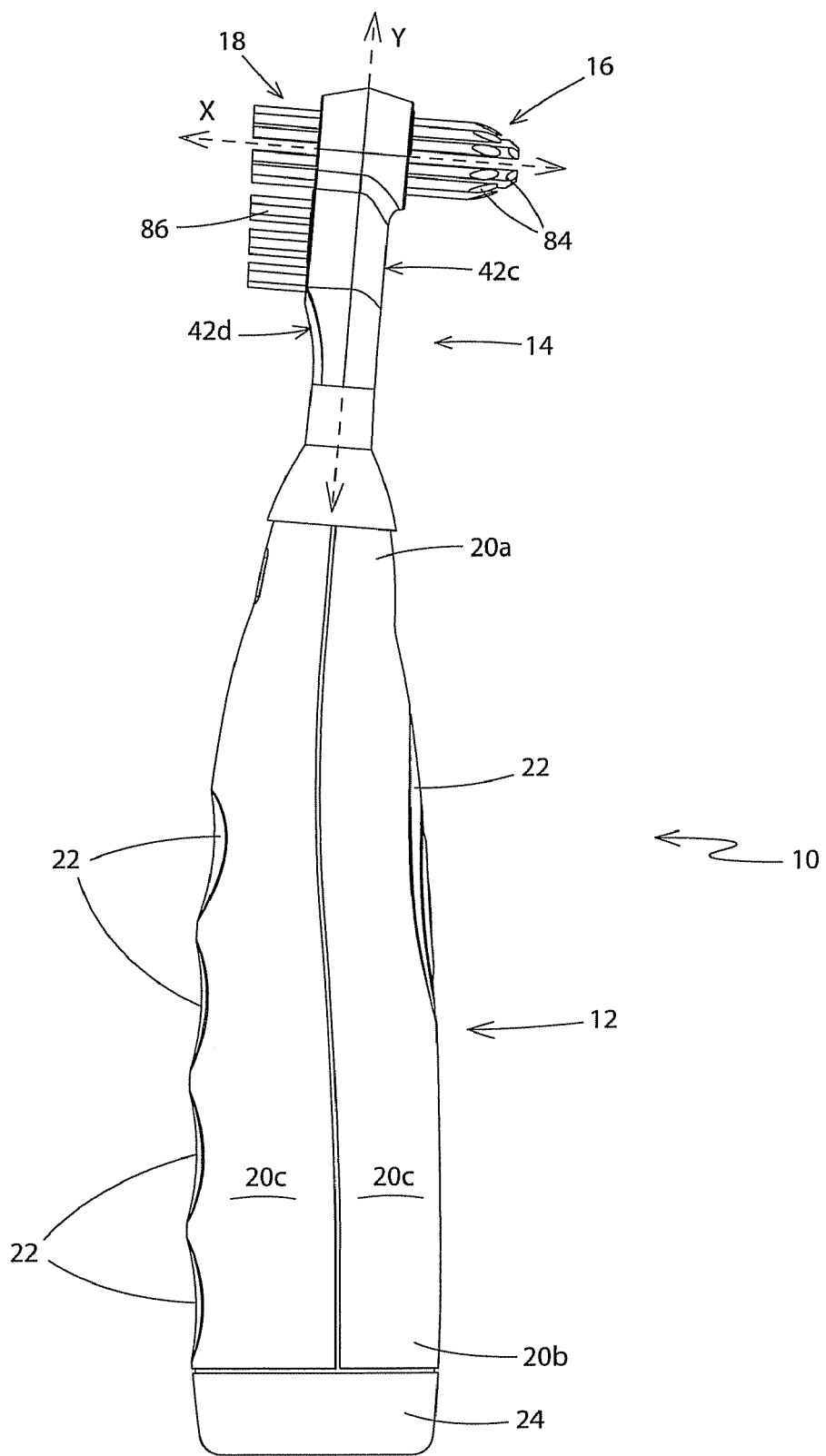
FIG. 4 is a right side elevational view of the denture brush.

Referring to FIGS. 1-5, handle 12 of the powered denture brush 10 in comprises a housing 20 having a front and a back that preferably are snap-fitted or otherwise secured together. Housing 20 has an upper end 20a, a lower end 20b and an exterior wall 20c extending therebetween. The front and back of housing 20 are molded and contoured in any suitable manner so that housing 20 may be easily gripped. Housing 20 preferably is also provided with a plurality of textured gripping surfaces 22 that may be manufactured from a different material to the rest of exterior wall 20c. Gripping surfaces 22 may be provided in some of the contoured regions such as the four finger placement regions on the back of housing 20 (FIG. 3). Gripping surfaces 22 and the contoured shape aid the user to more easily hold and manipulate handle 12. A removable cap 24 threadably engages lower end 20b. When cap 24 is removed, the user has access to an interior chamber 26 (FIG. 5a) for insertion or removal of batteries (not shown). An on/off button 28 is provided on a front of wall 20c to activate brush 10.

Figure 5A:
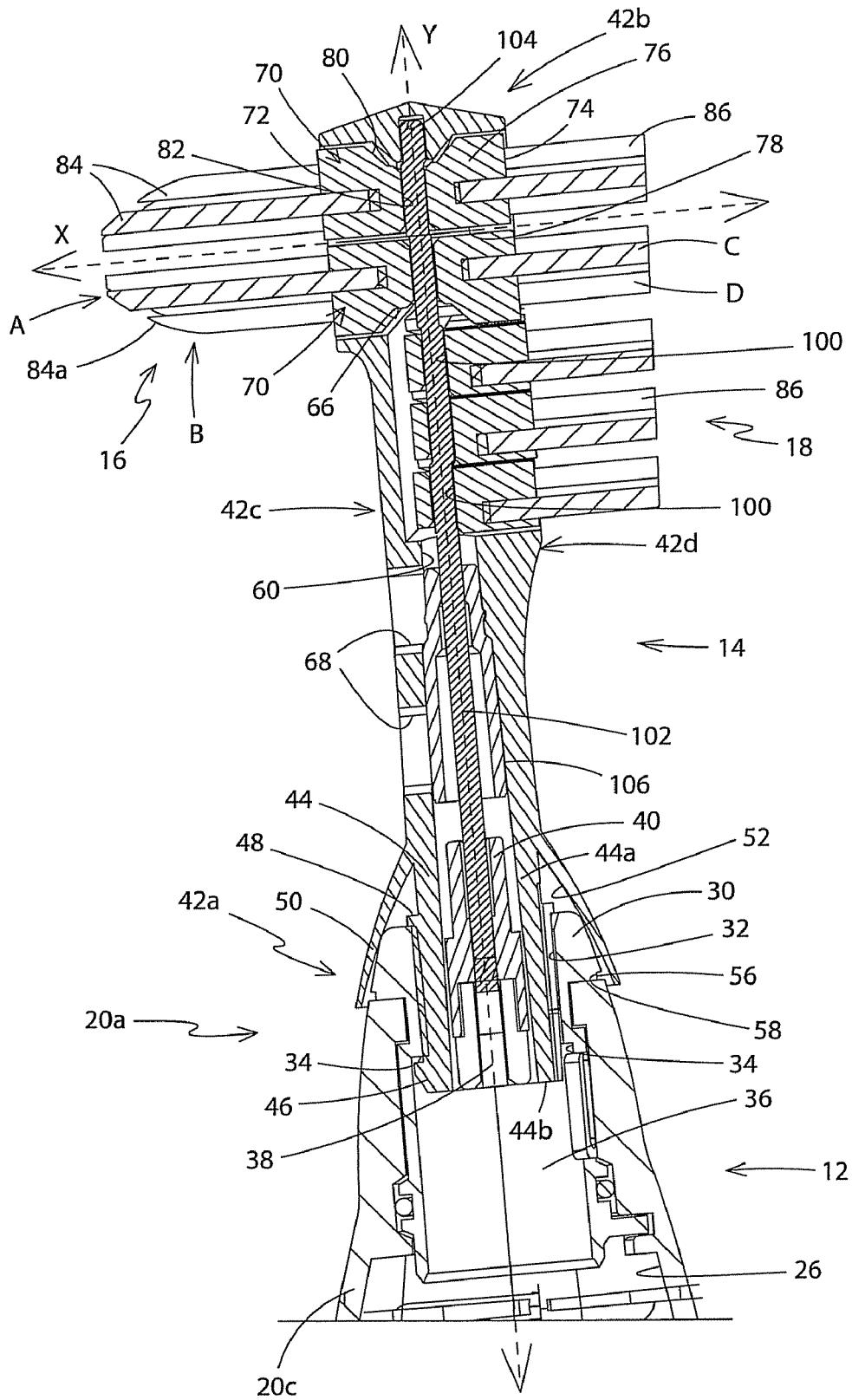
FIG. 5a is a cross-sectional left side view of the head of the denture brush with the camshaft in a first position.

The upper end 20a of handle 12 is configured to detachably engage with head 14. Referring to FIG. 5a, it will be seen that exterior wall 20c of handle 12 tapers toward upper end 20a ultimately terminating in a tip 30. Tip 30 defines a recess 32 therein. The interior surface of wall 20c forms an annular shoulder 34 that projects into recess 32. A motor 36, retained within interior chamber 26, is in operational communication with a power source (not shown) such as a rechargeable battery. Motor 36 is connected through circuitry (not shown) to the on/off button 28. A drive shaft 38 extends outwardly away from motor 36, through a portion of recess 32 and into operational engagement with a motor coupler 40.

Figure 5B:
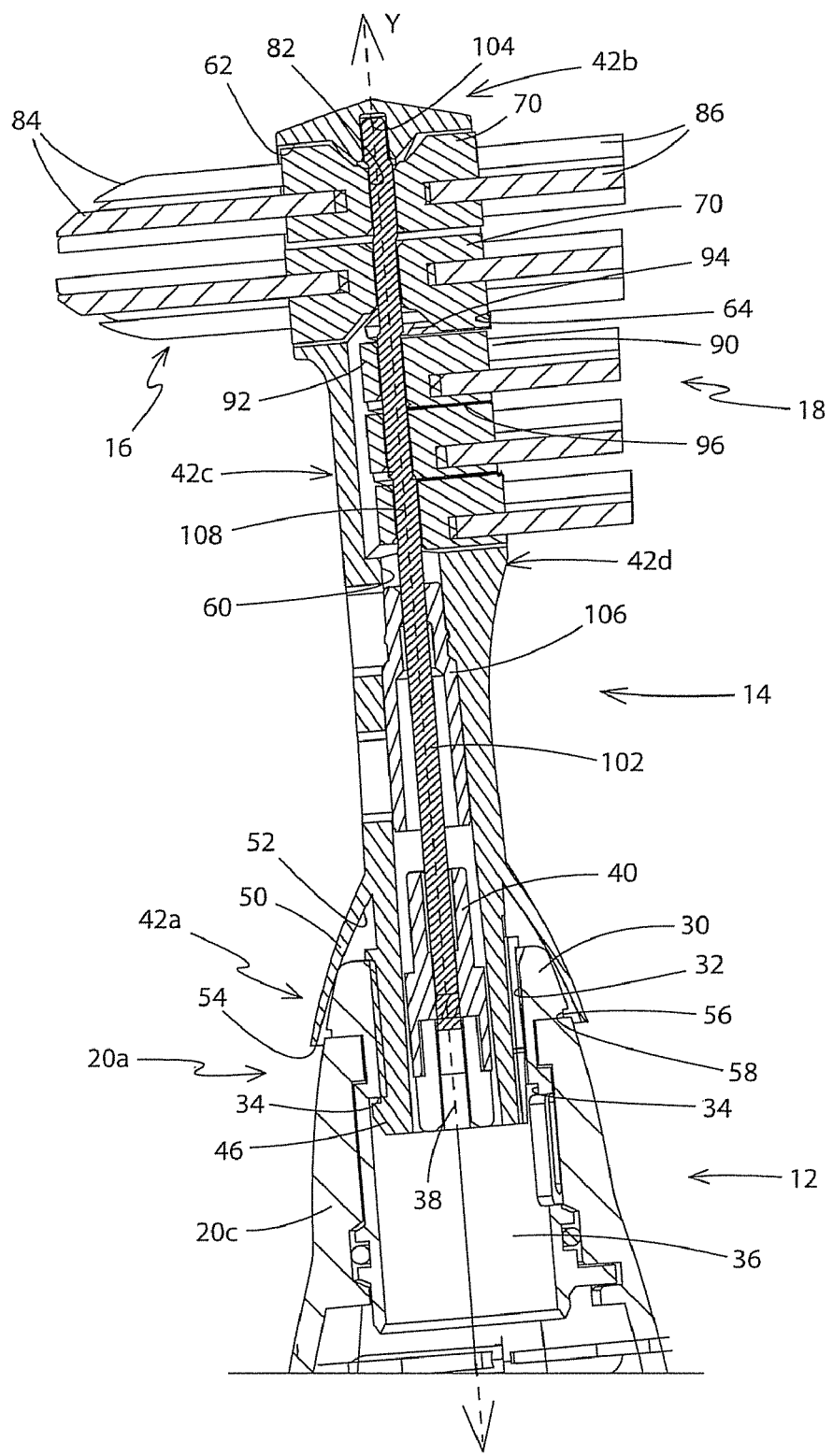
FIG. 5b is a cross-sectional left side view of the head of the denture brush showing the camshaft in a second position.
Figure 6:
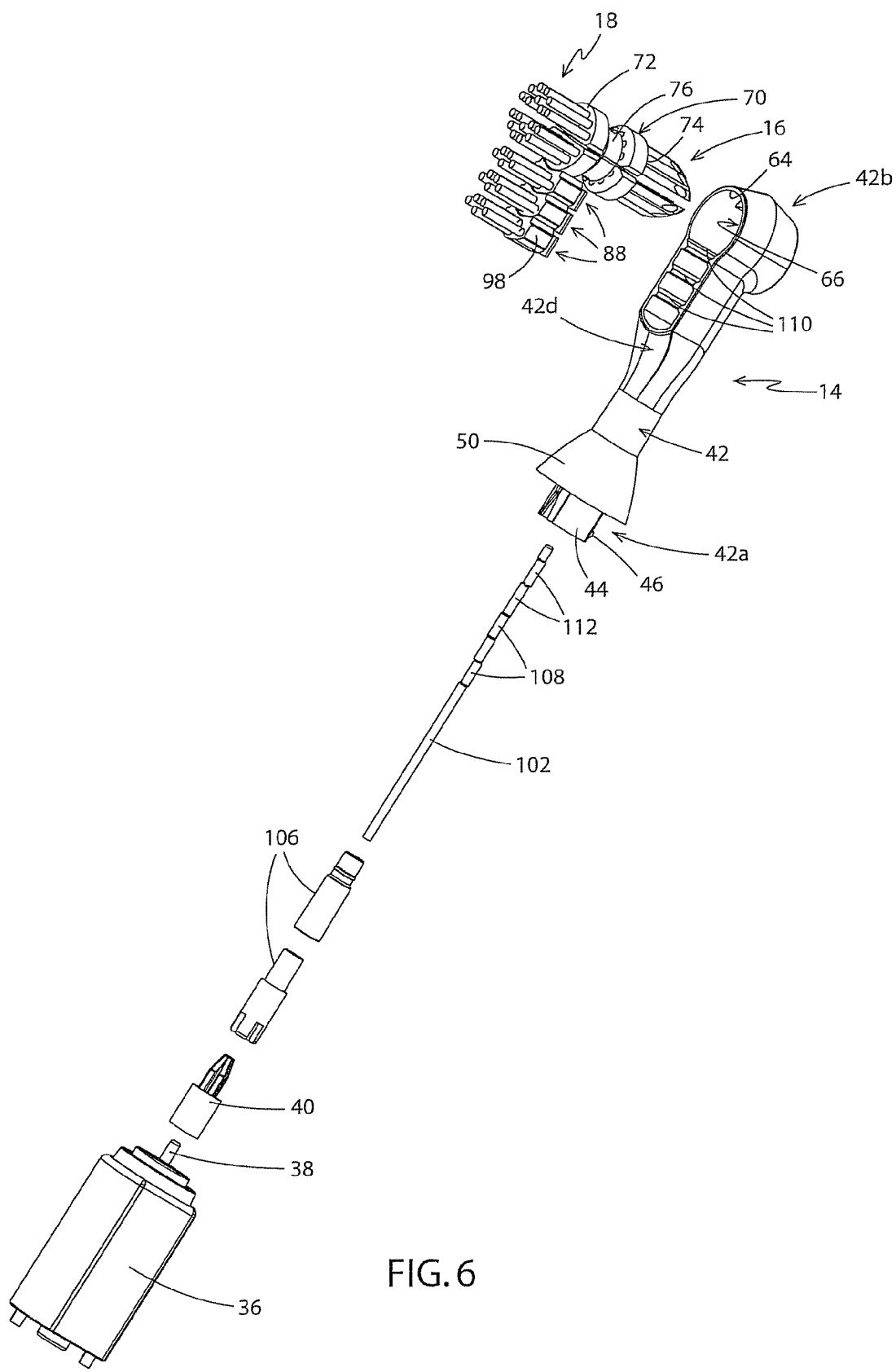
FIG. 6 is a partially exploded rear perspective view of the head of denture brush with the housing removed and showing the components that drive the camshaft.

Referring to FIGS. 5a, 5b and 6, head 14 of brush 10 comprises a housing 42 having a first end 42a and a second end 42b with a longitudinal axis "Y" (FIG. 2) that extends between the first and second ends 42a, 42b. Housing 42 also has a front face 42c and a rear face 42d with a horizontal axis "X" extending therebetween. The horizontal axis "X" is orthogonal to the longitudinal axis "Y". Housing 42 does not need to be very long as it in not designed for insertion into a person's mouth. First end 42a of housing 42 is configured to snap-fittingly engage with upper end 20a of handle 12. First end 42a includes a generally cylindrical, longitudinally aligned collar 44 that is complementary to recess 32 in handle 12. Collar 44 has an inner end 44a and an outer end 44b. Collar 44 includes a detent 46 that projects laterally outwardly away from collar 44 proximate outer end 44b and a flange 48 that projects laterally outwardly away from collar 44 proximate inner end 44a. Detent 46 is positioned on collar 44 in such a location that when collar 44 is inserted into recess 32, detent 46 interlocks with shoulder 34. Flange 48 is positioned on collar 44 in such a location that when collar 44 is inserted into recess 32, flange 48 abuts a portion of the tip 30 of first end 20a of handle 12. A portion of first end 20a is therefore wedged between flange 48 and detent 48 thereby preventing accidental disengagement of head 14 and handle 12.

First end 42a of head 12 further includes an annular skirt 50 that originates proximate inner end 44a of collar 44 and flares outwardly and downwardly away therefrom and toward outer end 44b. Skirt 50 terminates at an edge 54 spaced a distance inwardly from outer end 44b of collar 44. Skirt 50 is separated from collar 44 by a gap 52 that increases in size from proximate inner end 44a of collar 44 to edge 54 of skirt 50. Skirt 50 preferably is also provided with a lip 56 proximate edge 54 that extends laterally inwardly toward collar 44. When collar 44 is inserted into recess 32, skirt 50 slides downwardly over the exterior surface of upper end 20a of handle 12. Lip 56 interlocking engages in a groove 58 provided in upper end 20a of handle 12. This interlocking engagement aids in maintaining the connection between head 14 and handle 12.

Housing 42 of head 14 also defines a bore 60 (FIG. 5a) therein that extends from first end 20a to proximate second end 20b thereof. Bore 60 is substantially aligned with the longitudinal axis "Y". Housing 42 further defines a first aperture 62 (FIG. 2) in front face 42c proximate second end 20b. Housing 42 also defines a second aperture 64 (FIG. 3) in rear face 42d proximate second end 20b. First and second apertures 62, 64 are opposed to each other and are generally aligned along horizontal axis "X". First aperture 62 is generally circular in cross-sectional shape while second aperture 64 is generally shaped like a keyhole (see FIG. 6). First and second apertures 62, 64 are in communication with bore 60 such that a passageway 66 (FIG. 6) extends through head from front face 42c to rear face 42d. Housing 42 may also be provided with one or more openings 68 that permit fluid to flow into the interior of housing for cleaning of the same.

In accordance with a specific feature of the present invention, the second end 42b of housing 42 is provided with two sets of bristles, namely a first set of bristles 16 and a second set of bristles 18. The first set of bristles 16 extends outwardly away from front 42c of housing 42. The second set of bristles 18 extends outwardly away from back 42d of housing and in an opposite direction to first set of bristles 16. The bristles of each of the first and second sets 16,18 extend outwardly from second end 42b substantially parallel to horizontal axis "X" and are therefore disposed orthogonally to longitudinal axis "Y".

The first set of bristles 16 are secured to one or more first tuft blocks 70 that are mounted for movement between first and second apertures 62, 64 and in passageway 66 of housing 42. In accordance with a specific feature of the present invention, each first tuft block 70 is generally semicircular in cross-sectional shape and has a first exterior face 72 (FIG. 5a)

disposed proximate first aperture 62, a second exterior face 74 disposed proximate second aperture 64, and a body 76 that extends therebetween. Body 76 also has an interior face 78 and an exterior face 80. As shown in FIG. 6, preferably body 76 comprises two semicircular lobes separated by a semicircular saddle area thereinbetween. One of the lobes includes first exterior face 72 and the other of the lobes includes second exterior face 74. The saddle area is the region of a lesser radius that is located between the two lobes. FIG. 5a illustrates that a channel 82 extends through the saddle area of body 76 from the interior face 78 through to the exterior face 80. Channel 82 is oriented generally parallel to longitudinal axis "Y" of housing 42. As will be understood by those skilled in the art, the first tuft blocks 70 shown in FIGS. 5a-6 may alternatively be replaced by a single tuft block that is generally circular in cross-sectional shape and includes a channel that extends for the entire diameter of the saddle region between the two circular lobes. If two semicircular tuft blocks 70 are provided, the two blocks together form a substantially circular cross-sectional shape that is complementary to the circular first aperture 62. If only a single circular tuft block is provided, the cross-sectional shape of that block is complementary to the first aperture 62. It should be understood that if two semicircular first tuft blocks 70 are utilized, that these blocks are independently linearly slidable into and out of the first and second apertures 62, 64 and toward and away from front and rear faces 42c, 42d. Although not illustrated herein it will be understood that a pair of opposed guide rails may be provided within the passageway 66 that extends between first and second apertures 62, 64. These guide rails preferably would be disposed substantially orthogonal to the longitudinal axis "Y" of head 14 and would be disposed intermediate the planar interior faces 78 of blocks 70. The blocks 70 would then be slidable along said guide rails between first and second apertures 62, 64.

In accordance with another specific feature of the present invention, a plurality of first bristles 84 are secured to first exterior face 72. The plurality of first bristles 84 make up the first set of bristles 16 that extends outwardly away from front face 42c. First bristles 84 may be of any suitable type and may include a plurality of single bristles that are spaced apart from each other, or may be tufts of bristles that are secured in discrete groups that are spaced a distance apart from each other. When viewed from the front, the first bristles 84 on the two first tuft blocks 70 are arranged in a pattern of two or more concentric rings "A" and "B" (FIGS. 2 & 5a). (Obviously, each first tuft block 70 has its first bristles 84 arranged in two semicircular regions that together form the circular pattern). The innermost ring "A" includes a plurality of bristles 84 that are of a greater length than the plurality of bristles 84 that are in outermost ring "B". All or most of the bristles 84 in outermost ring "B" are provided with a truncated face 84a that is angled downwardly away from the tips of the longer bristles in ring "A" and toward front face 42c. Many of the bristles in innermost ring "A" are also provided with a truncated face. The arrangement of bristles 84 into the concentric rings and the physical shape of the bristles themselves allows them to fit easily into groove 504 of denture 500. The truncated faces of bristles 84 provides an increased bristle surface area to contact the bottom and sides of groove 504 at the same time and to better clean the same when brush 10 is activated, as will be hereinafter described.

A plurality of second bristles 86 make up part of the second set of bristles 18 that extend outwardly away from rear face 42d. Second bristles 86 are secured to second exterior face 74 of first tuft block 70. Second bristles 86 may, again, be of any suitable type and may include a plurality of single bristles that are spaced apart from each other, or may be tufts of bristles that are secured in discrete groups that are spaced a distance apart from each other. As was the case with the first bristles 84, the second bristles 86 are again arranged in a pattern of two or more concentric rings "C" and "D" (FIGS. 3 & 5a) when the brush 10 is viewed from the back. (Once again, the second bristles 86 on each of the semicircular tuft blocks 70 are arranged in a semicircular pattern). However, unlike first bristles 84, all of second bristles 86 are substantially of the same length and preferably none of the second bristles 86 have a truncated face. The shape, length and placement of second bristles 86 make them highly suitable for cleaning the teeth side 502 of denture 500 as they are able to chisel material off the teeth, get into the crevices between the teeth and sweep material out of contoured surfaces on the teeth.

In accordance with yet another feature of the present invention, head 14 is provided with one or more second tuft blocks 88 that are independently movable relative to each other and to the first tuft blocks 70. In the embodiment shown in the FIGS. 1-10, head 14 is provided with three second tuft blocks 88 that are substantially identical to each other. Unlike the first tuft blocks 70, the second tuft blocks 88 do not extend between or travel between the front and rear faces 42c, 42d of housing 42. Instead, second tuft blocks 88 are disposed within second aperture 64 and are mounted for travel into and out of second aperture 64 as will be hereinafter described. As shown in FIG. 5b, each second tuft block 88 has an external face 90, an internal face 92, a top face 94, a bottom face 96 and sides 98 (FIG. 6). The internal face 92 of each second tuft block 88 is disposed within bore 60. Each second tuft block 88 includes a channel 100 that extends between the top and bottom faces 94, 96 and is generally parallel to the longitudinal axis "Y" of the head 14. A plurality of second bristles 86 are secured to second tuft blocks 88 and extend outwardly away from external face 90 in a direction that is substantially parallel to horizontal axis "X". As shown in FIG. 3, second bristles 86 are arranged in a pattern of vertically aligned rows "E" along the three second tuft blocks 88. Once again, second bristles 86 may be individual bristles that are spaced apart from each other or may be tufts of bristles that are grouped together with the tufts being arranged in vertically aligned rows. The length of second bristles 86 in second tuft blocks 88 is substantially equal to the length of second bristles 86 in first tuft blocks 70.

Referring to FIG. 3, brush 10 preferably includes tufts of second bristles 86 on tuft blocks 88, with each individual tuft being of a first width. Each tuft block 88 further includes a plurality of individual tufts that are arranged generally in horizontal rows. The widest of these horizontal rows is of a second width. Furthermore, the individual tufts spanning the three tuft blocks 88 are arranged in generally vertical rows. The longest of these vertical rows across the three tuft blocks 88 is of a first length. Preferably the first length is around twice the size of the second width and is substantially larger than the first width.

Head 14 is provided with a camshaft 102 that is disposed within bore 60. Camshaft 102 is mounted at one end in a recess 104 (FIG. 5a) proximate second end 42b and is retained within bore 60 by one or more camshaft seals 106. Camshaft 102 terminates a short distance outwardly of outer end 44b of collar 44. Camshaft 102 is seated in camshaft seals 106 in such a manner that it is able to rotate through 360° within bore 60. When head 14 is engaged with handle 12, motor coupler 40 engages one of two camshaft seals 106 and operationally connects camshaft 102 to drive shaft 38. When motor 36 is activated by depressing button 28, the rotational motion imparted to drive shaft 38 is transferred to camshaft 102. Camshaft 102 is received through the channels 100 in second tuft blocks 88 and through the channels 82 in first tuft blocks 70. Camshaft 102 is provided with a plurality of spaced apart camming surfaces 108 that are offset relative to each other and are spaced so as to be positioned within channels 100. As camshaft 102 rotates, the camming surfaces 108 cause second tuft blocks 88 to slide linearly in and out of second aperture 64 in a direction parallel to horizontal axis "X" and orthogonal to longitudinal axis "Y. To aid in the sliding linear motion of second tuft blocks 88, housing 42 preferably is provided with a plurality of pairs of opposed guides 110 along which second tuft blocks 88 are able to slide. Guides 110 essentially comprise pairs of opposed flanges that extend inwardly from the wall that defines that portion of second aperture 64 that houses second tuft blocks 88.

In accordance with a specific feature of the present invention, camshaft 102 is additionally provided with camming surfaces 112 that are received within the channels 82 of first tuft blocks 70. The rotation of camshaft 102 causes first tuft blocks 70 to slide linearly in and out of both of the first and second apertures 62, 64. This linear motion is in a direction that is parallel to the horizontal axis "X" and orthogonal to the longitudinal axis "Y".

Brush 10 is used in the following manner. The user depresses button 28 to activate motor 36. Motor 36 causes drive shaft 38 and therefore camshaft 102 to rotate about the longitudinal axis "Y". The rotation of camshaft 102 causes second tuft blocks 88 to slide linearly in and out of second aperture 64 and away and toward rear face 42*d* of housing 42. The brush 10 is brought into the vicinity of denture 500. The orientation of the brush is selected based on whether the user intends cleaning the teeth side 502 of denture 500 or the groove side 504 thereof. If the teeth side 502 is selected, the user will orient the brush 10 in the manner shown in FIG. 9 so that the second set of bristles 18 is brought into contact with the teeth 502. The pulsing action of second tuft blocks 88 causes the second bristles 86, which extend outwardly therefrom, to effectively chisel material off the teeth 502. As the camshaft 102 rotates, it also causes a pulsing action in the first tuft blocks 70 as these first tuft blocks slide linearly in and out of the first and second apertures 62, 64 and toward and away from both of the front and rear faces 42*c*, 42*d* of brush 10. Consequently, if brush 10 is oriented so that the second set of bristles 18 contacts the teeth side 502 of denture 500, then the second bristles 86 on the pulsing first tuft blocks 70 also chisels material off the teeth.

Effectively, activation of the brush 10 causes both of the first and second sets of bristles 16, 18 to be set in motion. Consequently, when the user wishes to clean the groove side 504 of denture 500, they merely flip the brush 10 over so that the first set of bristles 16 is received within the groove 504 of the denture 500. The pulsing action of the first tuft blocks 70 moving linearly toward and away from the front face 42*c* of brush 10 effectively chisels and sweeps unwanted material out of groove 504 with minimal effort being expended by the user. The simultaneous activation of the motion in the first and second bristles 16, 18 is advantageous because the user is then able to merely flip the brush 10 over in order to engage the appropriate one of the first and second sets of bristles 16, 18 with the appropriate side of the denture 500. There is no need for the user to operate a number of different switches in order to accomplish the cleaning task. They are able to merely switch the brush on once and can flip the brush over any number of times during the cleaning operation and then switch the brush off again when the task is completed.

Figures 7A, 7B:
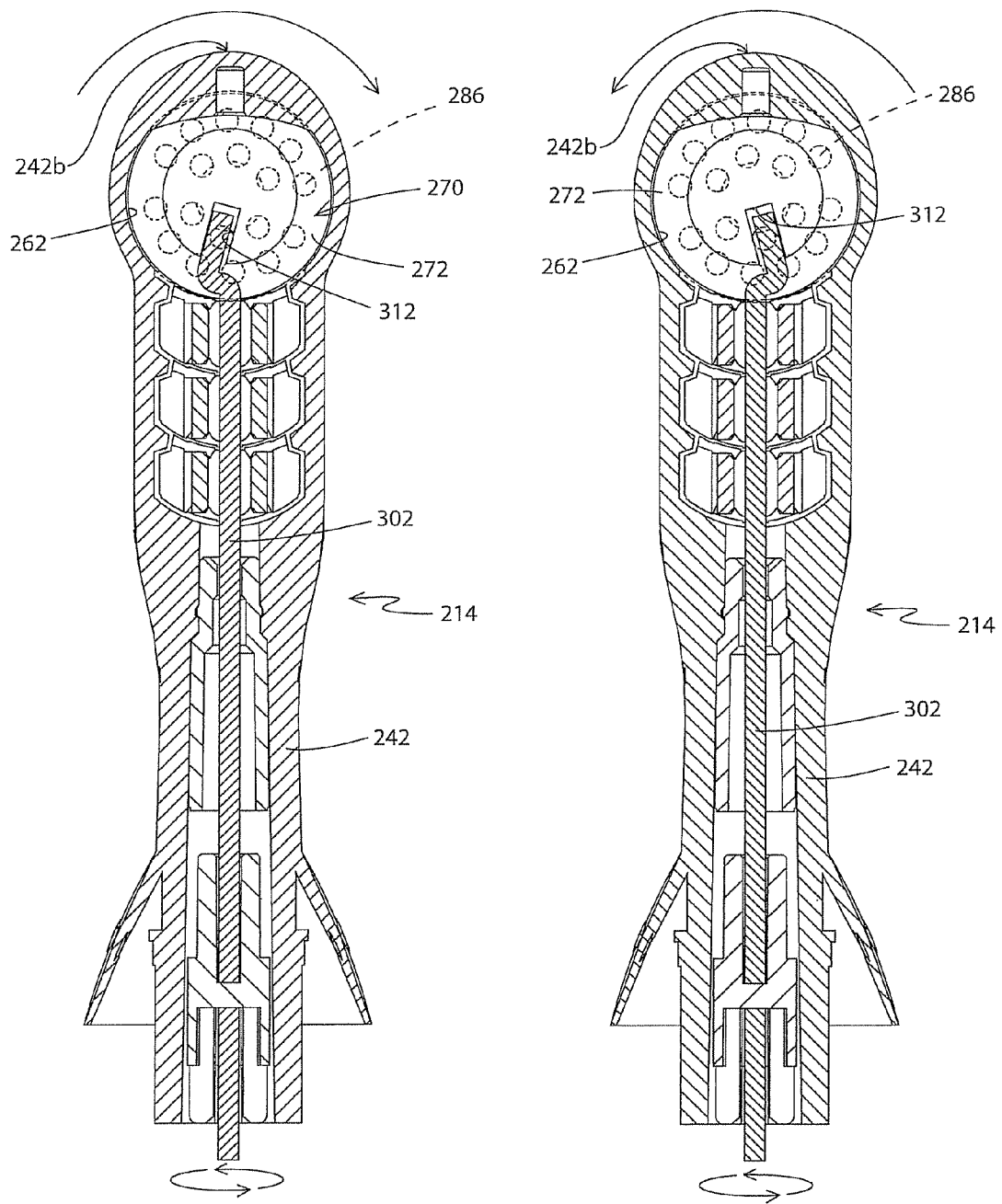
FIG. 7a is a cross-sectional front view of a second embodiment of the head of a powered denture brush in accordance with the present invention showing the rotation of the first tuft block in a first direction in response to rotation of the camshaft.
FIG. 7b is a cross-sectional front view of the head of FIG. 7a, showing the rotation of the first tuft block in a second direction in response to rotation of the camshaft.
Figure 8:
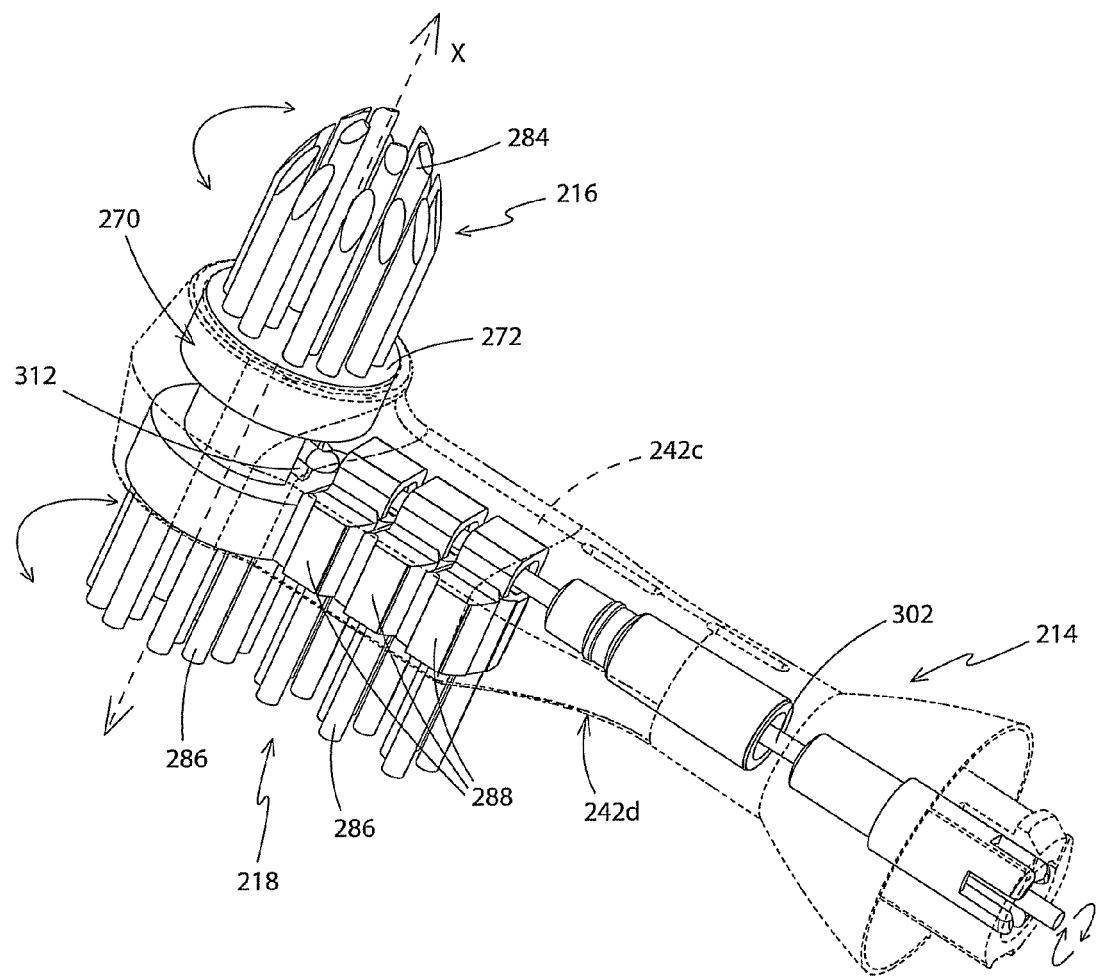
FIG. 8 is a front perspective view of the head of FIGS. 7a and 7b with the housing shown in phantom.
Figure 9:
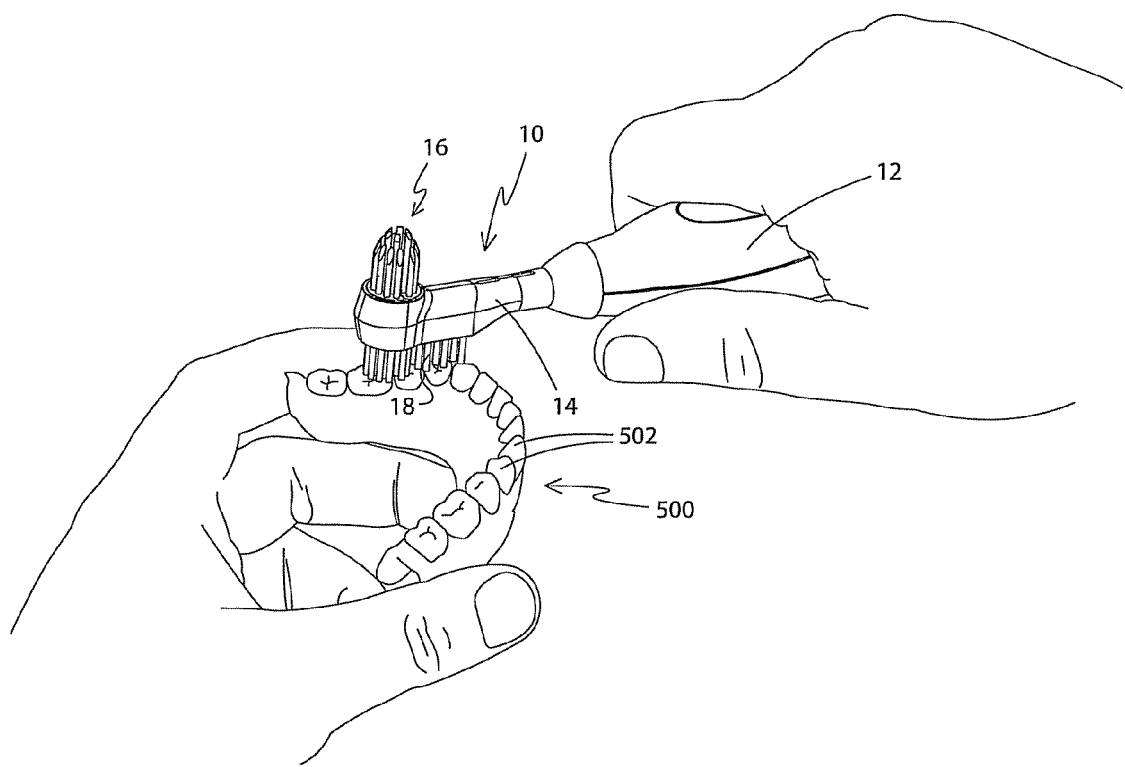
FIG. 9 is a perspective view of the denture brush showing a first set of bristles being used to clean the teeth side of the denture.

FIGS. 7*a*, 7*b* and 8 show a second embodiment of the head of a powered denture brush in accordance with the present invention, with the head being generally referenced by the number 214. Head 214 is configured to be snap fitted to a powered handle such as handle 12 described previously herein. Head 214 is substantially identical to head 14 with the exception that there is a single first tuft block 270 that is substantially circular in cross sectional shape and that the camshaft 302 terminates in an angled slot 312 in first tuft block 270 instead of in a recess proximate the second end 242*b* of housing 242 as was the case with the previous embodiment. Consequently, when camshaft 302 is rotated by the drive shaft, first tuft block 270 is caused to rotate about the horizontal axis "X" (FIG. 8) instead of being linearly sliding in and out of the first aperture 262. The rotation of first tuft block 270 about horizontal axis "X" is illustrated in FIGS. 7*a* and 7*b*. The first tuft block 270 therefore oscillates between a first and second position and causes the first and second bristles 284, 286 of the first and second sets of bristles 216, 218 on first tuft block 270 to move in an arcuate path as is shown by the arrows in FIGS. 7*a*, 7*b* and 8. The first tuft block 270 will rotate back and forth through an arc of between 30° and 50°. Preferably, the first tuft block 270 will rotate through an arc of about 40°.

The second tuft blocks 288 are caused to slide linearly into and out of the second aperture (not shown) in the rear face 242*d* of housing 242 and in the same manner as was previously described with reference to the first embodiment. It should be understood that because the camshaft 302 is causing both the rotational motion of first tuft block 270 and the linear sliding motion of second tuft blocks 288, that the rotational and linear motion occurs substantially simultaneously. Consequently, some of the second bristles 286 (those on first tuft block 270) move in an oscillating arcuate path across the teeth 502 while others of the second bristles 286 (those on second tuft blocks 288) pulse in and out of the housing 242. The pulsating movement occurs in a direction parallel to the horizontal axis "X" and it occurs at the same time as the rotational or oscillating motion. In use, the powered denture brush is therefore able to both chisel material from teeth 502, by way of bristles 286 on second tuft blocks 288, and sweep material from teeth 502 by way of bristles 286, 284 on first tuft block 270. This makes the brush far more effective as a cleaning tool. Additionally, the rotational movement of the first set of bristles 216 within the groove 504 of denture 500 effectively sweeps unwanted materials from the groove 504.

Preferably the motor coupler 40, camshaft seal 106, the housings 20 and 42 of the handle 12 and head 14 and the tuft blocks 70 and 88 are all manufactured from Acrylonitrile Butadiene Styrene (ABS) plastic resin and the camshaft is manufactured from stainless steel.

Although not illustrated herein, it will be understood that the head of the present invention may include one or more stationary, nonmoving bristle that extends outwardly away from one or both of the first and second sides of the head. These stationary bristles preferably will extend outwardly away from the side and be disposed substantially orthogonally relative to the longitudinal axis of the head. Additionally, the second tuft blocks 88, 288 may be omitted and replaced with entirely stationary bristles without departing from the spirit of the present invention.

It will be understood that while the camshaft 302 is provided with camming surfaces that engage the tuft blocks 288 and cause them to slide into and out of the second aperture in the head, the camshaft 302 may, alternatively, be devoid of camming surfaces in locations along its length that correspond to one or more of said tuft blocks 288. In this latter instance, when the camshaft rotates, those tuft blocks 288 would remain stationary and would not move into and out of the second aperture.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A powered denture brush for cleaning a denture where the denture has a grooved side for receiving gum tissue therein and a teeth side opposed therefrom; said denture brush comprising:
   a handle having a powered drive member mounted therein;
   a brush head having a first end and a second end and a longitudinal axis extending therebetween; wherein said first end is detachably engageable with said handle, and said second end includes:
      a first set of bristles extending outwardly away from a first side of the second end; said first set of bristles being adapted to clean the groove side of the denture; and wherein at least some of said first set of bristles are mounted for movement relative to the first side in response to operation of said drive member; and
      a second set of bristles extending outwardly away from a second side of the second end; said second set of bristles being adapted to clean the teeth side of the denture, and wherein at least some of said second set of bristles are mounted for reciprocal linear movement toward and away from said second side in response to the operation of said drive member.

2. The denture brush as defined in claim 1, wherein the first side of the head defines a first aperture therein and the brush further includes a first tuft block disposed for movement within said first aperture in response to the operation of the drive member; and wherein the at least some of the first set of bristles are secured to a first exterior face of the first tuft block and extend outwardly away therefrom and substantially parallel to a horizontal axis disposed orthogonally to the longitudinal axis.

3. The denture brush as defined in claim 2, wherein the first tuft block is slidably mounted for reciprocal linear movement through the first aperture and toward and away from said first side in response to the operation of the drive member, said linear movement being oriented substantially parallel to the horizontal axis.

4. The denture brush as defined in claim 3, wherein the second side of the second end defines a second aperture therein in a position opposed to the first aperture; and the head further defines a passage connecting the first and second apertures; and wherein said first tuft block is disposed within said passage such that said first exterior face is positioned proximate the first aperture and said first tuft block includes a second exterior face positioned proximate the second aperture; and wherein at least some of the second set of bristles are secured to the second exterior face of the first tuft block and extend outwardly away therefrom substantially parallel to the horizontal axis and in a direction opposite to the first set of bristles extending outwardly from the first exterior face; and wherein the first tuft block moves linearly toward and away from each of the first and second sides and orthogonally to the longitudinal axis of the head.

5. The denture brush as defined in claim 4, wherein the first aperture is substantially circular in cross-sectional shape and the first tuft block is substantially circular in cross-sectional shape and is complementary to the first aperture.

6. The denture brush as defined in claim 4, wherein the at least some of the first set of bristles are secured in the first exterior face of the first tuft block in a pattern comprising at least two concentric rings, and wherein the bristles in an innermost one of the rings are longer than the bristles in an outermost one of the rings.

7. The denture brush as defined in claim 4, wherein the first aperture is substantially circular in cross-sectional shape and the first tuft block comprises two substantially identical blocks that are each semicircular in cross-sectional shape; and wherein the two blocks are received within the first aperture such that the overall cross-sectional shape of the two blocks together is complementary to the first aperture; and wherein the two blocks are mounted for independent movement relative to each other into and out of the first and second apertures and toward and away from the first and second sides of the head, and wherein some of the bristles of the first set of bristles are secured to a first exterior face of each of the two blocks, and some of the bristles of the second set of bristles are secured to a second exterior face of each of the two blocks.

8. The denture brush as defined in claim 4, wherein the first tuft block defines a channel therein which is disposed generally parallel to the longitudinal axis of the head and spaced generally midway between the first and second exterior faces of the first tuft block; and wherein the brush further includes:
   an interior bore that extends from the first end of the head to proximate the second end thereof; and
   a camshaft extends through said bore and is operationally connected at one end to the drive member in the handle; and wherein the camshaft includes at least one camming surface that is received within the channel of the first tuft block, whereby rotation of the camshaft in response to the operation of the drive member causes the linear movement of the first tuft block.

9. The denture brush as defined in claim 8, further comprising at least one second tuft block mounted for linear reciprocal movement into and out of the second aperture only and relative to the second side of the head, said movement being substantially parallel to the horizontal axis; and wherein at least others of the second set of bristles are secured to an exterior face of the second tuft block and extend outwardly therefrom parallel to the horizontal axis and in a direction opposite to the first set of bristles.

10. The denture brush as defined in claim 9, further comprising at least one pair of spaced apart, opposed guides provided in a wall that defines said second aperture, said guides being oriented substantially parallel to the horizontal axis and being disposed intermediate the first and second tuft block.

11. The denture brush as defined in claim 10, wherein the second set of bristles disposed at least partially on each of the first and second tuft blocks are all substantially of the same length.

12. The denture brush as defined in claim 11, wherein the second tuft block defines a channel therein that is spaced a distance inwardly from the exterior face thereof, said channel being oriented substantially parallel to the longitudinal axis of the head; and wherein the camshaft includes at least a second camming surface and said camshaft extends through the channel in the second tuft block such that the second camming surface is disposed within the second tuft block, and wherein rotation of the camshaft causes the linear reciprocal movement of the second tuft block into and out of the second aperture and said movement is independent of the movement of the first tuft block.

13. The denture brush as defined in claim 2, wherein the first tuft block is mounted for reciprocal rotational movement within the first aperture, said rotation being oriented around the horizontal axis.

14. The denture brush as defined in claim 13, wherein the first tuft block rotates through an arc of between 30° and 50°.

15. The denture brush as defined in claim 13, wherein the second side of the second end defines a second aperture therein in a position opposed to the first aperture; and the head further defines a passage connecting the first and second apertures; and wherein said first tuft block is disposed within said passage such that said first exterior face thereof is positioned proximate the first aperture; and said first tuft block further includes a second exterior face positioned proximate the second aperture; and wherein at least some of the second set of bristles are secured to the second exterior face and extend outwardly away therefrom substantially parallel to the horizontal axis and in a direction opposite to the first set of bristles.

16. The denture brush as defined in claim 15, wherein the first tuft block defines an angled channel therein, said channel being generally disposed midway between the first and second exterior faces; and wherein the brush further includes:
   an interior bore that extends from the first end of the head to proximate the second end thereof;
   a camshaft extending through said bore and being operationally connected at one end to the drive member in the handle and terminating at the other end in the angled channel in the first tuft block; wherein rotation of the camshaft in response to the operation of the drive member causes rotational movement of the first tuft block about the horizontal axis.

17. The denture brush as defined in claim 16, further comprising a second tuft block mounted for linear reciprocal movement into and out of the second aperture and relative to the second side of the head, said linear movement being substantially parallel to the horizontal axis; and wherein at least others of the second set of bristles are secured to an exterior face of the second tuft block and extend outwardly therefrom parallel to the horizontal axis and in a direction opposite to the first set of bristles.

18. The denture brush as defined in claim 17, further comprising at least one pair of spaced apart, opposed guides provided in a wall that defines said second aperture, said guides being oriented substantially parallel to the horizontal axis and being disposed intermediate the first and second tuft blocks.

19. The denture brush as defined in claim 18, wherein at least some of the first set of bristles are secured in the first exterior face of the first tuft block in a pattern comprising at least two concentric rings, and wherein the bristles in an innermost one of the rings are longer than the bristles in an outermost one of the rings; and wherein the bristles of the second set of bristles on the second exterior face of the first tuft block are arranged in a pattern of one or more concentric rings with the bristles in an innermost one of the rings being substantially the same length as the bristles in an outermost one of the rings.

20. The denture brush as defined in claim 19, wherein the others of the second set of bristles provided on the exterior face of the second tuft block are arranged in aligned rows, and the bristles in the aligned rows are substantially of the same length as the bristles of the second set of bristles in the concentric rings.

21. The denture brush as defined in claim 1, wherein the head defines a longitudinally aligned bore extending between the first and second ends of the head; said bore being open at the first end of the head; and wherein an interior wall of the second end of the head defines a longitudinally-aligned hole that is of a smaller diameter than the bore; and wherein the brush further includes a camshaft received within the bore; and a first end of said camshaft is operationally connected to the drive member, and a second end of the camshaft is received within the hole.

22. The denture brush as defined in claim 1, wherein the head includes:
   a collar extending outwardly away from the first end of the head and parallel to the longitudinal axis thereof; said collar having an inner end unitary with the first end of the head and an outer terminal end spaced a distance away therefrom, said collar including a generally cylindrical wall disposed between the inner and terminal ends thereof; and
   an annular skirt member originating proximate the inner end of the collar and extending downwardly toward the outer end thereof; said skirt member flaring outwardly away from the collar wall whereby an increasing gap is disposed between the skirt member and the wall.

23. The denture brush as defined in claim 22, wherein the handle has an upper end configured to engage the first end of the brush, said upper end of the handle including a longitudinally aligned recess in which the drive member is disposed; and an exterior wall that tapers inwardly proximate the upper end; and wherein the collar extending from the first end of the head is received in the recess and the skirt member engages the exterior wall of the handle.

24. The denture brush as defined in claim 1, wherein the head includes a plurality of holes therein, said holes being adapted to permit liquid to flow through an interior chamber in the head for cleaning of the same.

25. The denture brush as defined in claim 1, wherein one or both of the first and second sides of the head may further include at least one stationary bristle that extends outwardly away from the one of the first and second sides and substantially orthogonal to the longitudinal axis of the head.

26. A detachable head for a powered denture brush; wherein said head comprises:
   a housing having a first end and a second end and a longitudinal axis extending therebetween; said first end being adapted to be detachably engaged with a powered handle, and wherein said second end of the housing includes:
      a first set of bristles extending outwardly away from a first side of the second end; said first set of bristles being adapted to clean a groove side of a denture; and wherein at least some of said first set of bristles are mounted for movement relative to the first side in response to operation of a drive member in the handle; and
      a second set of bristles extending outwardly away from a second side of the second end; said second set of bristles being adapted to clean a teeth side of the denture, and wherein at least some of said second set of bristles are mounted for reciprocal linear movement toward and away from said second side in response to the operation of said drive member.

27. The detachable head for a denture brush as defined in claim 26, wherein the at least some of the first set of bristles are mounted for reciprocal linear movement toward and away from said first side of the housing in response to the operation of the drive member.

28. The detachable head for a denture brush as defined in claim 26, wherein the at least some of the first set of bristles are mounted for reciprocal rotational movement relative to the first side of the housing; and wherein said rotation takes place about a horizontal axis disposed at right angles to the longitudinal axis of the housing and occurs in response to the operation of the drive member.

29. The detachable head for a denture brush as defined in claim 28, wherein at least others of the second set of bristles are mounted for reciprocal rotational movement relative to the second side of the housing; and wherein said rotation takes place about the horizontal axis and in response to the operation of the drive member.

30. The detachable head for a denture brush as defined in claim 29, wherein the rotational motion of the at least some of the first set of bristles and at least others of the second set of bristles, occurs simultaneously with the reciprocal linear movement of at least some of the second set of bristles.

* * * * *